US00PP25999P3

(12) United States Plant Patent
Gargiulo

(10) Patent No.: US PP25,999 P3
(45) Date of Patent: Oct. 20, 2015

(54) GRAPEVINE PLANT NAMED 'CAR2-21-20'

(50) Latin Name: *Vitis vinifera*
Varietal Denomination: CAR2-21-20

(71) Applicant: M. CARATAN, INC., Delano, CA (US)

(72) Inventor: Angel A. Gargiulo, Mendoza (AR)

(73) Assignee: M. Caratan, Inc., Delano, CA (US)

( * ) Notice: Subject to any disclaimer, the term of this patent is extended or adjusted under 35 U.S.C. 154(b) by 99 days.

(21) Appl. No.: 13/998,802

(22) Filed: Dec. 9, 2013

(65) Prior Publication Data

US 2015/0163976 P1 Jun. 11, 2015

(51) Int. Cl.
*A01H 5/00* (2006.01)

(52) U.S. Cl.
USPC ..... Plt./207

(58) Field of Classification Search
USPC ..... Plt./207
See application file for complete search history.

*Primary Examiner* — Annette Para
(74) *Attorney, Agent, or Firm* — Jondle & Associates, P.C.

(57) ABSTRACT

A new and distinct variety of grapevine plant named 'CAR2-21-20' particularly distinguished by very large berry size, very large berry clusters, uniformly filled clusters and strong berry attachment, is disclosed.

5 Drawing Sheets

Genus and species: *Vitis vinifera.*
Variety denomination: 'CAR2-21-20'.

BACKGROUND OF THE NEW PLANT

The present invention comprises a new and distinct variety of grapevine botanically known as *Vitis vinifera* and hereinafter referred to by the variety name 'CAR2-21-20'. The new variety originated from a cross conducted in September 1994 in Salta de las Rosas, Mendoza, Argentina between the female grapevine plant named 'Majestic' (unpatented) and the male grapevine plant named '552' (U.S. Plant Pat. No. 9,916). A single plant was selected for further evaluation and asexual propagation.

The new variety was first propagated in 2005 in Davis, Calif. by vegetative cuttings and has been asexually reproduced repeatedly by vegetative cuttings for four generations. 'CAR2-21-20' has been found to retain its distinctive characteristics through successive asexual propagations.

Plant Breeder's Rights for this variety have not been applied for. 'CAR2-21-20' has not been made publicly available anywhere in the world more than one year prior to filing of this application.

SUMMARY OF THE INVENTION

The following are the most outstanding and distinguishing characteristics of this new variety when grown under normal horticultural practices in Delano, Calif.

1. Very large berry size;
2. Very large clusters;
3. Uniformly filled clusters; and
4. Strong berry attachment.

DESCRIPTION OF THE PHOTOGRAPHS

This new grapevine plant is illustrated by the accompanying photographs which show clusters of fruit, leaves, canes, tendrils and berries. The colors shown are as true as can be reasonably obtained by conventional photographic procedures. The photographs are taken from a mature plant about 5 years old, grown in a field in Delano, Calif. under natural light.

Figure 1:
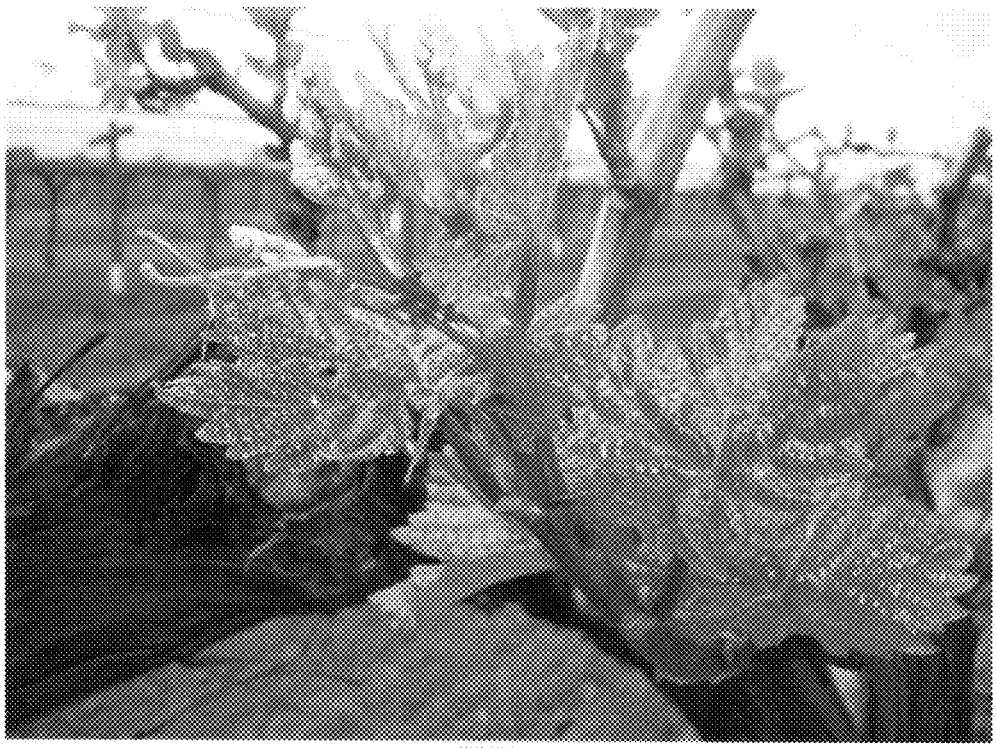
Figure 2:
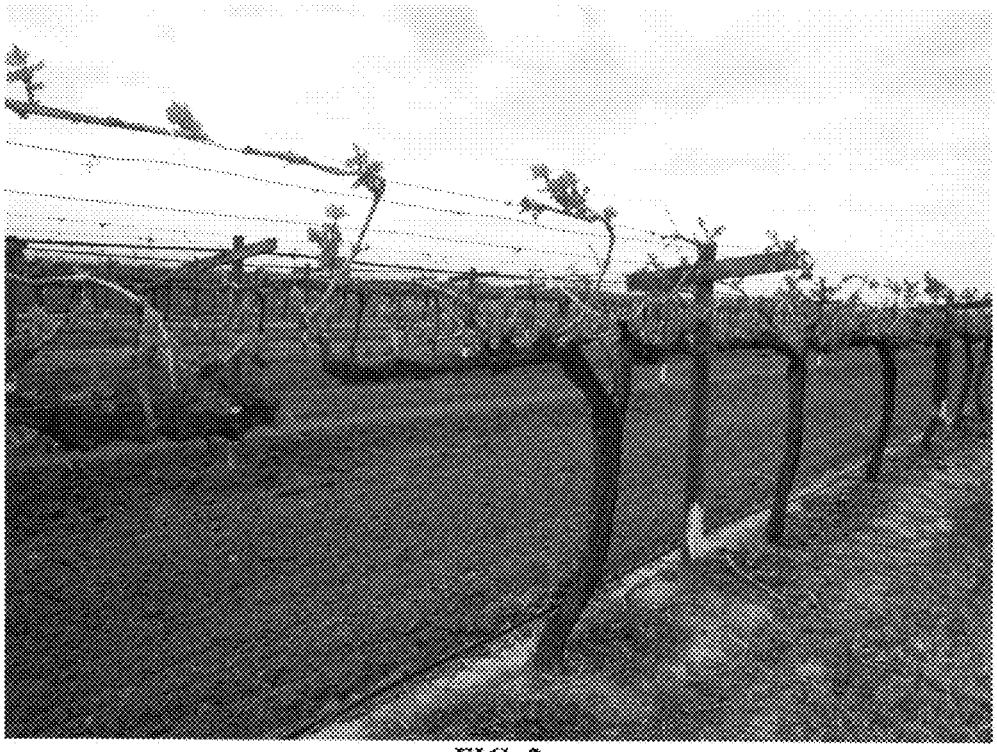
Figure 3:
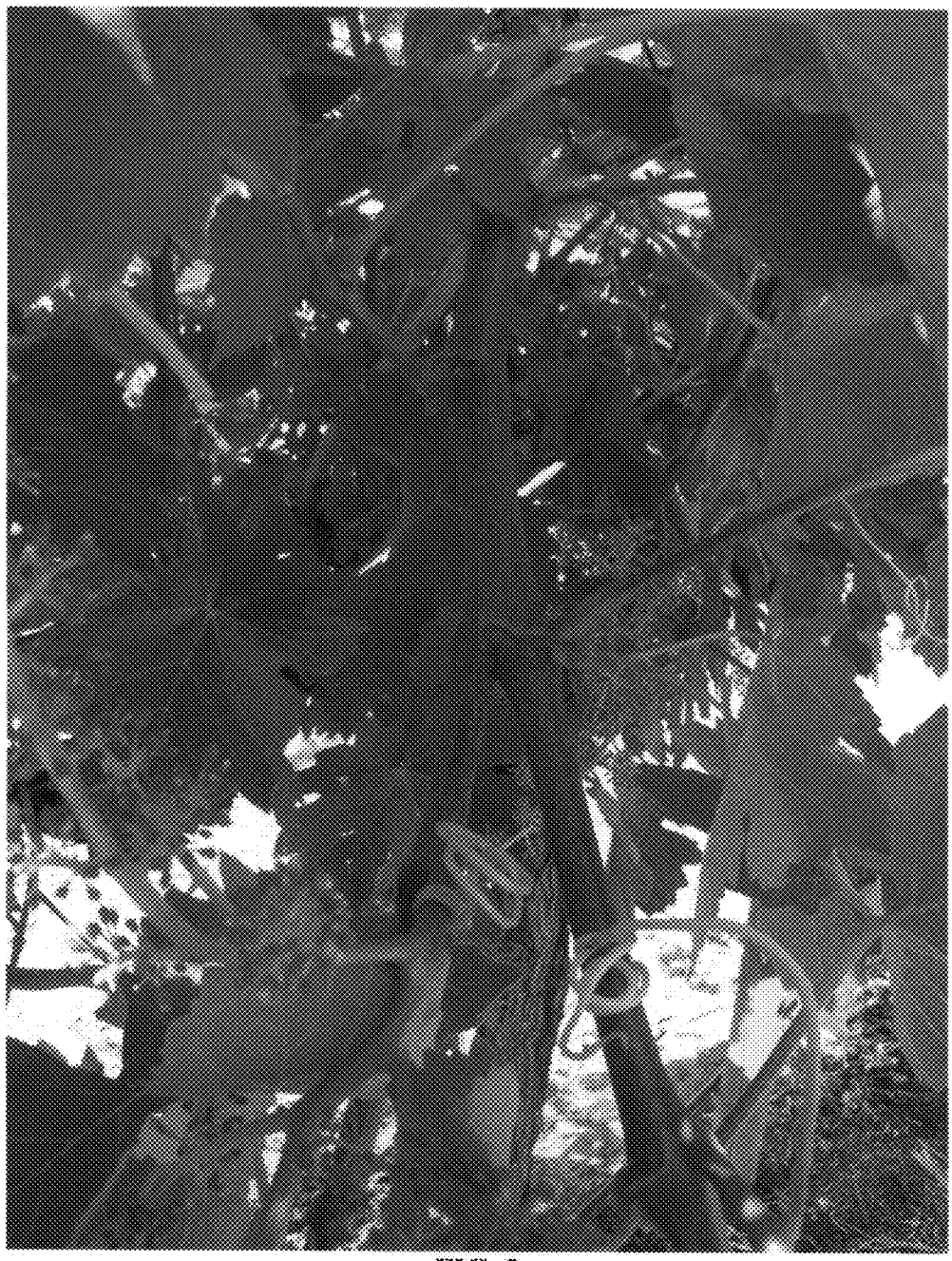
Figure 4:
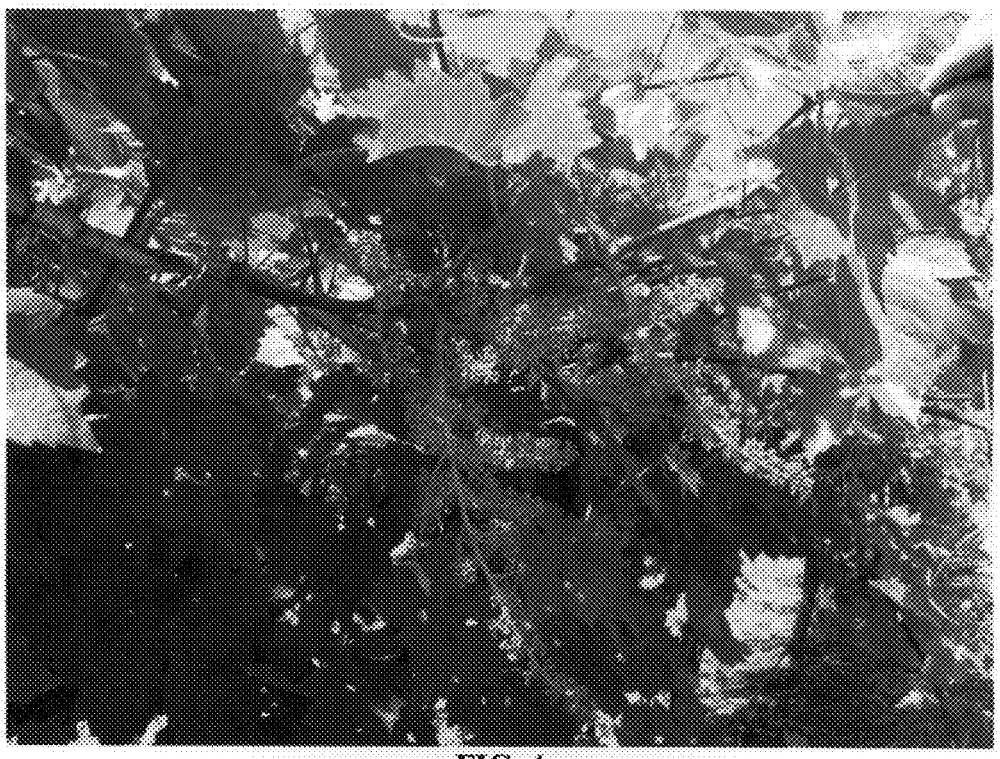
Figure 5:
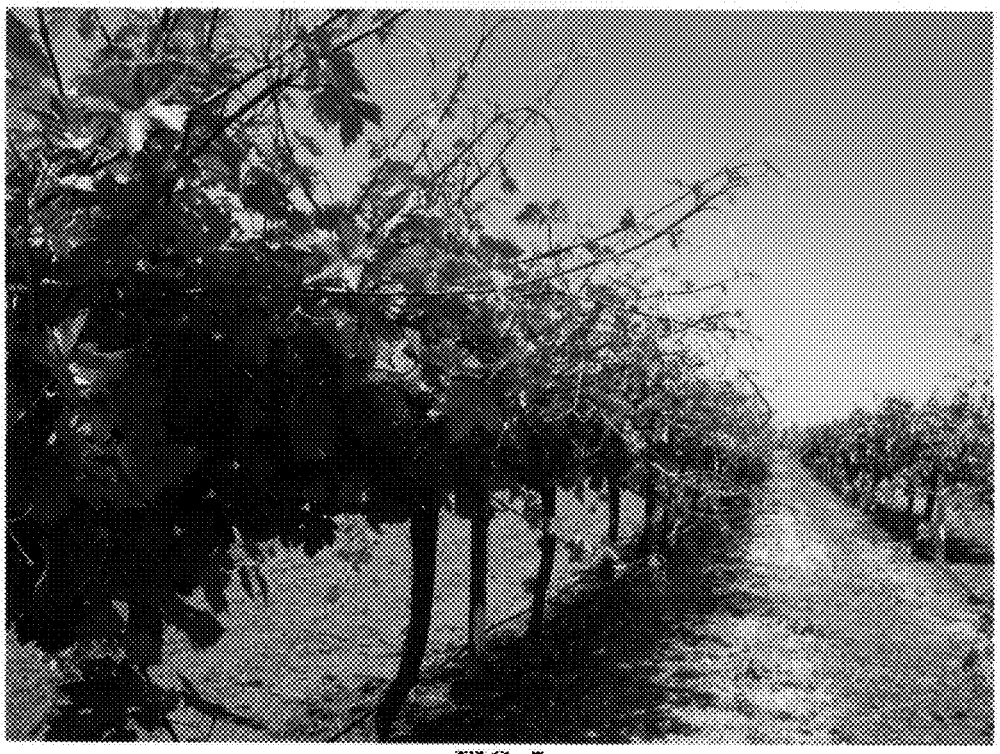
Figure 6:
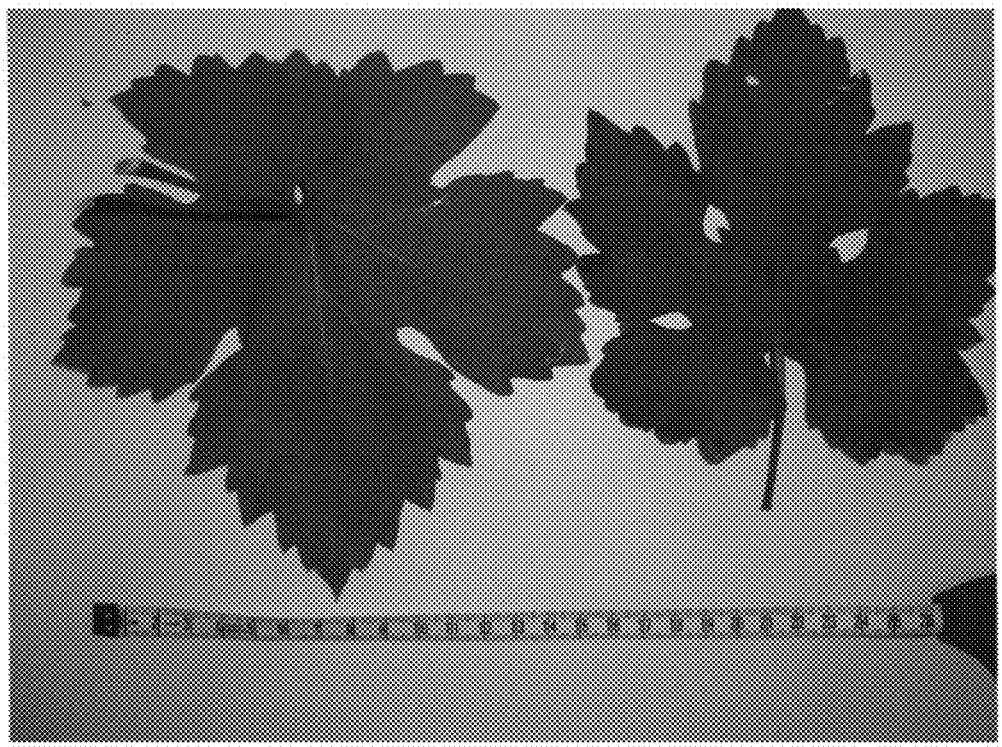
Figure 7:
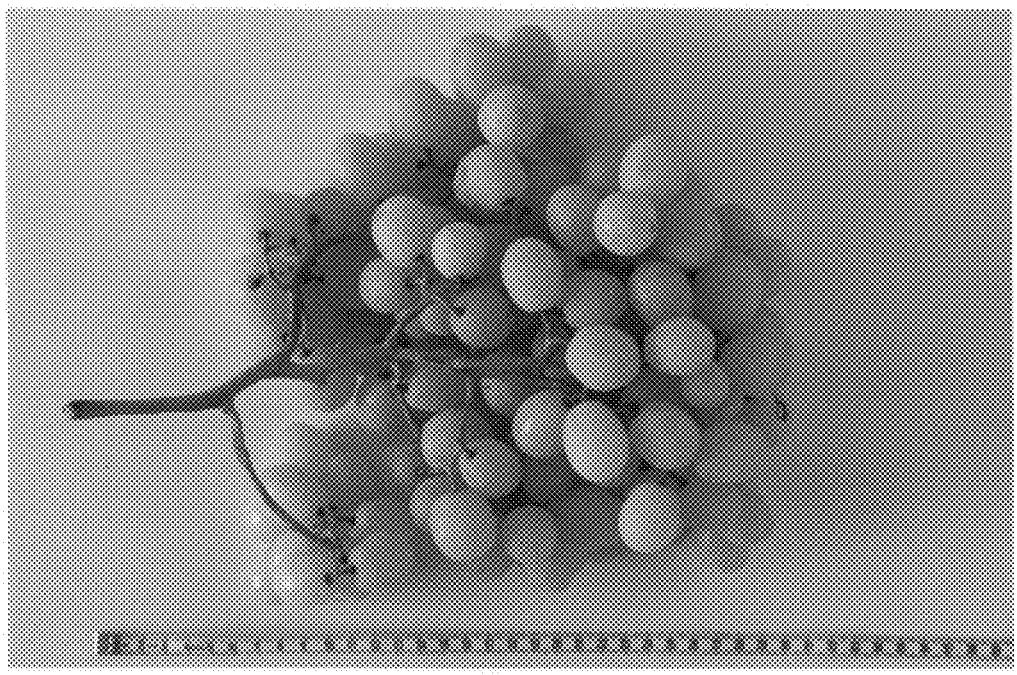
Figure 8:
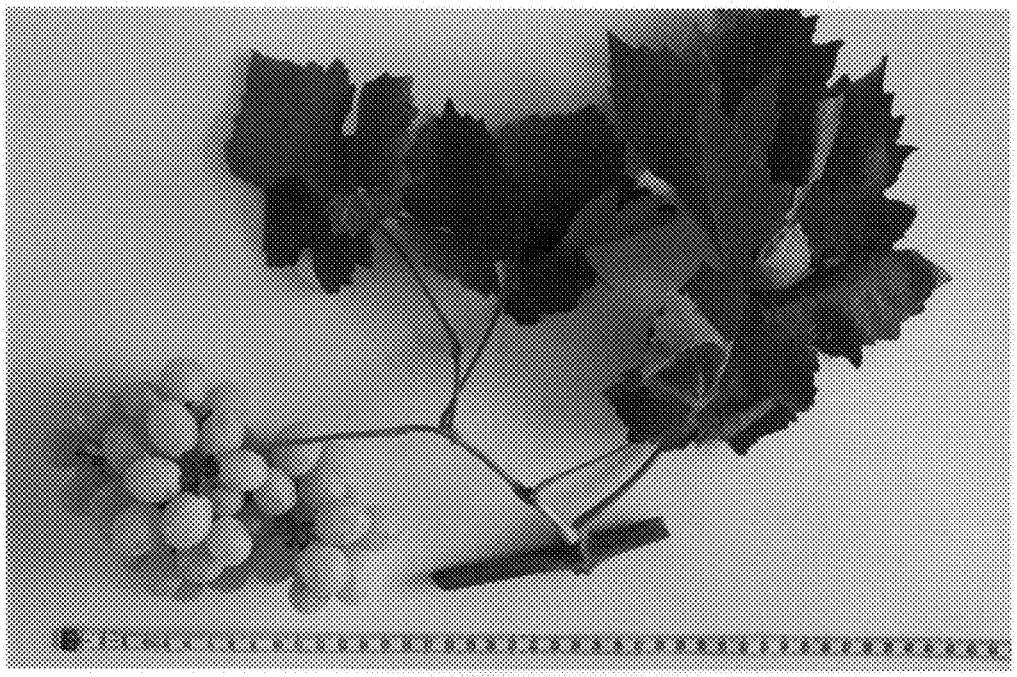
Figure 9:
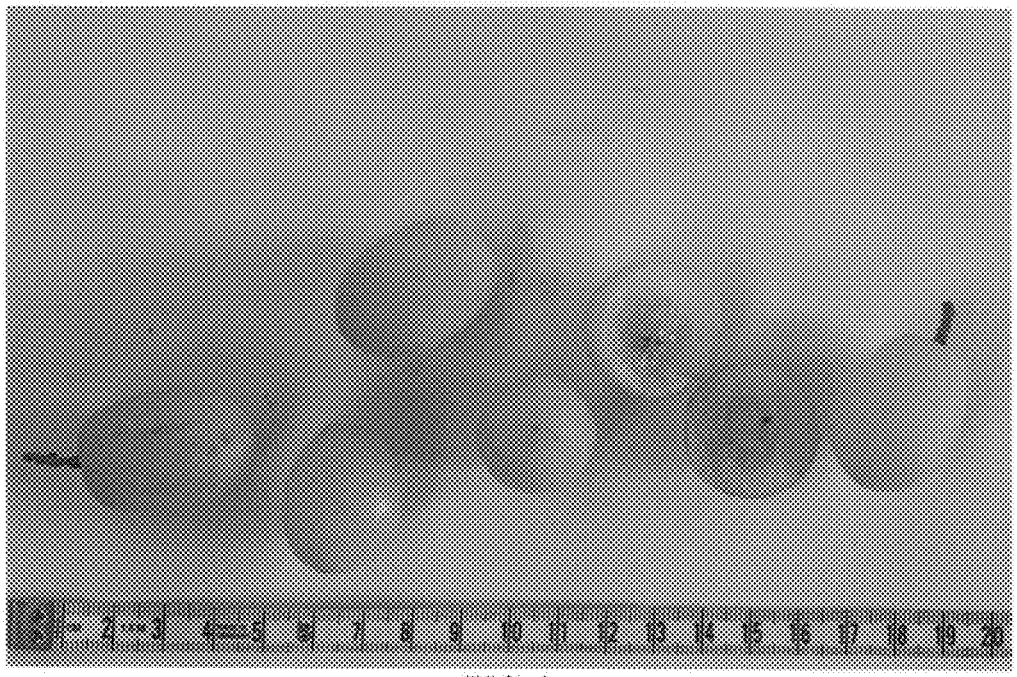

FIG. 1 shows growing leaf tips and immature leaves.
FIG. 2 shows leaves with budbreak complete.
FIG. 3 shows a bifurcated primary shoot.
FIG. 4 shows a floral cluster in full bloom.
FIG. 5 shows plants during grand period of growth.
FIG. 6 shows upper and lower surfaces of mature leaves.
FIG. 7 shows a mature berry cluster commercially tipped with two inside laterals removed.
FIG. 8 shows a secondary cluster and leaves.
FIG. 9 shows a close-up of mature berries and aborted seeds.

DESCRIPTION OF THE NEW VARIETY

The following detailed descriptions set forth the distinctive characteristics of 'CAR2-21-20'. The data which defines these characteristics were collected from asexual reproductions carried out in Delano, Calif. The plant history was taken on mature 5 year old grapevines grown under field conditions in Delano, Calif. All color references were obtained under natural light. Color references are primarily to the Munsell Color Charts for Plant Tissues by Munsell Color, 617 Little Britain Rd., New Windsor, N.Y. 12553-6148, 1977 edition. Common color names are also occasionally employed.

DETAILED BOTANICAL DESCRIPTION OF THE NEW PLANT

Classification:
*Family.*—Vitaceae.
*Botanical name.*—*Vitis vinifera.*
*Variety name.*—'CAR2-21-20'.

Parentage:
*Female parent.*—'Majestic' (unpatented).
*Male parent.*—'552' (U.S. Plant Pat. No. 9,916).

Plant:

*Plant habit and growth.*—Trailing growth; secondary shoots are sparse and most show little growth; occasional bifurcated primary shoot.

*Size.*—Large; canopy filling an expansive trellis.

*Time to maturity.*—3 to 4 years.

*Height* (*at maturity; from floor*).—Cordon: 120.0 cm. Canopy: 195.0 cm.

*Width* (*at maturity*).—220.0 cm (row spacing 360 cm).

*Vigor.*—High.

*Productivity.*—High.

*Rootstock.*—Vines are own rooted.

Trunk:

*Diameter.*—8.7 cm.

*Surface texture.*—Rough.

*Color.*—Exposed surface: 10R 5/2. Non-exposed: 10R 5/6.

Canes:

*Diameter* (*measured between nodes* 4 *and* 5).—Average 11.0 mm.

*Length.*—Average 97.5 cm.

*Surface texture* (*both immature and mature canes*).—Smooth.

*Form* (*woody shoot cross section form*).—Pith between nodes with diaphragm at nodes.

*Color* (*mature at* 3 *months*).—5YR 5/6.

*Color* (*immature at* 6 *weeks*).—2.5GY 7/6. Anthocyanin: 5R 4/6.

*Internode length* (*upper mature sun cane*).—Average 10.0 cm taken at mid-section of canes. Number of nodes: Average 18 nodes per cane.

Time of bud burst (50% of buds broken): Mar. 30, 2013 (The 2013 budbreak in Delano, Calif. was approximately 7 days ahead of an average year).

Tendrils:

*Form.*—Mostly trifid.

*Size.*—General: Large. Length (average): 35.0 cm to 42.0 cm on mature canes. Diameter (measured at base of tendril): 3.0 mm to 4.0 mm.

*Texture.*—Smooth.

*Distribution.*—Discontinuous. Predominate sequence: No tendril, tendril, tendril, no tendril, tendril, tendril, no tendril, tendril, tendril.

*Color* (*mature;* 5 *weeks old*).—2.5GY 8/8. Anthocyanin: 10R 4/8.

*Color* (*immature,* 2 *weeks old*).—2.5GY 8/8. Anthocyanin: 10R 4/8.

Growing tips (young shoot):

*Pubescence.*—Sparse.

*Color.*—2.5GY 6/8.

*Anthocyanin.*—10R 4/10.

*Shape.*—Fully open.

*Apex.*—Normal, triangular.

Leaves:

*Shape.*—Pentagonal.

*Apex.*—Pointed.

*Base.*—Rounded.

*Margin.*—Irregular teeth.

*Height of teeth on margin.*—5.0 mm to 10.0 mm.

*Shape of teeth on margin.*—Convex.

*Texture* (*mature leaf*).—Upper surface: Dull, smooth, glabrous. Lower surface: Smooth, glabrous.

*Immature leaf.*—Length: 6.5 cm at fourth node from shoot tip at 8 to 10 days old. Width: 6.0 cm at 8 to 10 days old. Color: Upper surface: 5GY 6/6. Anthocyanin: 10R 5/8. Lower surface: 5GY 6/6. Anthocyanin: 10R 5/8.

*Mature leaf.*—Length: 17.0 cm at ninth node from shoot tip at 20 days old. Width: 18.0 cm at ninth node from shoot tip at 20 days old. Color: Upper surface: 5GY 5/6. Lower surface: 5GY 6/6.

*Venation.*—Pattern: Primary and secondary veins on the upper surface are visible due to their lighter color contrasting with the interveinal tissue; the lower surface veins are raised. Color: Upper surface: 2.5GY 7/6. Anthocyanin: Toward base 10R 4/10. Lower surface: 2.5GY 7/6. Anthocyanin: Toward base 10R 4/10.

*Petiolar sinus.*—Slightly overlapped.

*Petiole.*—Length: 8.0 cm. Diameter: 3.0 mm. Color: 10R 5/6.

Floral cluster:

*General description and location.*—Large wide laterals with occasional prominent wing and occasional peduncle tendril. Floral clusters are mostly on the $4^{th}$ node (occasionally on the $3^{rd}$ node), and it is not uncommon to have 2 clusters per shoot on the $4^{th}$ and $5^{th}$ node.

*Quantity of inflorescences per cluster* (*average*).—600 to 800 per cluster.

*Length* (*not including the peduncle*).—Average 29.0 cm.

*Width.*—Average 29.0 cm.

*Peduncle.*—Length: Average 29.0 cm. Width: Average 6.0 mm.

*Inflorescences.*—Hermaphroditic.

*Stamens.*—Upright. Length: 2.5 mm.

*Anthers.*—Russet in center and creamy white on outside.

*Date of bloom.*—Full bloom on May 7, 2013 (In the Delano, Calif. area the 2013 bloom occurred about 10 days ahead of an average year).

*Pollen amount.*—Moderate. Color: Pale creamy white.

*Calyptra.*—Description: 5 segments with complete separation. Color: 5GY 6/6.

Fruit:

*Time of year of commercial harvest and shipment.*—Mid-September to mid-October.

*Cluster* (*primary bunches*).—General size: Large. Weight: Average 1500.0 g. Length (without peduncle): 30.0 cm. Width: 20.0 cm. Density: Medium. Peduncle length: 4.0 cm. Peduncle diameter: 8.0 mm. Peduncle color: 5GY 7/8. Number of berries per cluster: 125. Berry: Size: Large; 12.0 g. Shape: Broad ellipsoid. Uniformity: High uniformity. Brix content: 15° on Aug. 29, 2013; 18.5° on Oct. 3, 2013. Diameter: 27.0 mm. Length: 33.0 mm. Skin color: 2.5GY 8/6. Pedicel: Length: 12.0 mm. Diameter: 2.0 mm. Color: 5GY 7/6. Strength of attachment to berry: Very strong.

*Cluster* (*secondary bunches*).—General size: Medium. Length (without peduncle): 9.5 cm. Width: 10.0 cm. Density: Medium. Peduncle length: 6.5 cm. Peduncle diameter: 2.0 mm. Peduncle color: Mostly pigmented 2.5 GY 8/6. Anthocyanin: 10R 5/8. Number of berries per cluster: Average 38. Berry: Size: Medium. Weight: 2.0 g. Shape: Broad ellipsoid. Uniformity: High. Brix content: 4.5° on August $29^{th}$. Diameter: 12.0 mm. Length: 15.0 mm. Skin color: 5GY 7/8.

Pedicel: Length: 8.0 mm. Diameter: 1.0 mm. Color: 7.5GY 7/6. Strength of attachment to berry: Strong.

Berry flesh:

*Color*.—5Y 8/2.

*Juice*.—Color: Clear. Production: Light.

*Thickness of skin*.—Medium and firmly attached to flesh.

*Flavor*.—Neutral.

*Fragrance*.—Neutral.

*Texture*.—Medium to firm.

Seeds: Mostly 1 to 2 aborted seeds per berry; some berries have no aborted seeds; difficult to detect when eating berry.

*Length*.—5.0 mm.

*Width*.—3.5 mm.

*Color*.—2.5Y 8/6.

*Firmness*.—Very soft.

Disease and insect resistance: No particular resistance or susceptibility has been observed. Normal disease control practices can be used.

COMPARISON WITH PARENTAL AND COMMERCIAL VARIETIES

'CAR2-21-20' differs from the female parent grapevine plant named 'Majestic' (unpatented) in that 'CAR2-21-20' has large, white berries with strong berry attachment, whereas 'Majestic' has medium, red berries with medium berry attachment.

'CAR2-21-20' differs from the male parent grapevine plant named '552' (U.S. Plant Pat. No. 9,916) in that 'CAR2-21-20' has white berries with minimal splitting and strong berry attachment, whereas '552' has red berries that are prone to splitting and have low to medium berry attachment.

'CAR2-21-20' differs from the commercial grapevine plant named 'Autumn King' (U.S. Plant Pat. No. 16,284) in that 'CAR2-21-20' has broad ellipsoid berries with a uniform berry size and very large berry clusters averaging 0.9 kg, whereas 'Autumn King' has cylindrical to ovoid berries with a mixed berry size and medium sized berry clusters averaging 0.5 kg. Additionally, 'CAR2-21-20' ripens in September and contains fewer aborted seeds than 'Autumn King', which ripens in October.

I claim:

1. A new and distinct variety of grapevine plant named 'CAR2-21-20' as shown and described herein.

* * * * *